(12) United States Patent
Van et al.

(10) Patent No.: US 6,567,541 B1
(45) Date of Patent: May 20, 2003

(54) METHOD AND APPARATUS FOR ADHESION TESTING OF THIN FILM MATERIALS

(75) Inventors: Phuc Van, San Jose, CA (US); Yuen Lim, San Jose, CA (US)

(73) Assignee: Ahbee 1, L.P., San Jose, CA (US)

( * ) Notice: Subject to any disclaimer, the term of this patent is extended or adjusted under 35 U.S.C. 154(b) by 0 days.

(21) Appl. No.: 09/512,787

(22) Filed: Feb. 25, 2000

(51) Int. Cl.⁷ .................................................. G06K 9/00
(52) U.S. Cl. ........................................ 382/145; 438/16
(58) Field of Search ........................... 382/145; 29/833; 438/16; 118/666, 708, 712, 713; 427/10; 204/298.03; 356/369

(56) References Cited

U.S. PATENT DOCUMENTS

| | | | | |
|---|---|---|---|---|
| 4,177,372 A | * | 12/1979 | Kotera et al. ................. | 117/39 |
| 4,905,319 A | * | 2/1990 | Schroder et al. ............. | 505/191 |
| 5,143,896 A | * | 9/1992 | Harada et al. ............... | 118/708 |
| 5,240,180 A | * | 8/1993 | Feuillerat et al. ........ | 239/132.3 |
| 5,955,139 A | * | 9/1999 | Iturralde ........................ | 427/9 |

FOREIGN PATENT DOCUMENTS

| | | | |
|---|---|---|---|
| GB | 2269799 | * | 2/1994 |
| JP | 3-56846 | * | 3/1991 |
| JP | 2001-220688 | * | 8/2001 |
| WO | WO 98/51754 | * | 11/1998 |

* cited by examiner

*Primary Examiner*—Samir Ahmed

(57) ABSTRACT

An apparatus for the automatic testing the adhesion characteristics of thin film and coating to silicon wafers, and the processing of the data obtained thereby to present to the user a rapid and accurate forecast of the thin film's behavior in a selected processing environment. The apparatus of the invention heats and cools samples while automatically monitoring for debonding. Information collected from the optical and thermal devices are processed by computer for analysis and recorded for cataloging. Information is collected and processed over time while samples are subjected to selected temperature environments to provide a data base of adhesion characteristics of thin films and coatings.

22 Claims, 12 Drawing Sheets

METHOD AND APPARATUS FOR ADHESION TESTING OF THIN FILM MATERIALS

BACKGROUND OF THE INVENTION

The present invention relates to material testing. More Particularly, the present invention relates to the testing of adhesion properties of thin film materials.

The microelectronics industry is ever increasing the density of components to meet cost and performance demands of the consumer. Reliability and service life are of concern to both the industry and customers. One technology trying to meet those demands is thin film technology. The industry is researching the application of various new materials to meet the low dielectric constant requirement for improved back-end of line interconnect performance.

Successful application of the new materials requires maintaining mechanical integrity, including fracture resistance, throughout the multilayering processes. The adhesion of grown and deposited films must be excellent to ensure good reliability and service life of the resulting products. In most cases, adhesion is strongly affected by the cleanliness of the substrate. Contamination of interfaces results in reduced adhesion, as does an adsorbed gas layer. Substrate surface roughness can promote adhesion, but may also result in coating defects.

Adhesion of thin films and coatings to various materials is of importance when they are subjected to various conditions or processes. Because electronic devices are fabricated from a variety of materials using silicon substrates and various applied films, stresses develop between layers as a result of expansion mismatches between the laminations. Poor adhesion represents a potential reliability problem. If films lift from the substrate, device failure can result.

The adhesion of thin films is particularly important in the microelectonics industry where devices are subjected harsh conditions. With the industry drive toward smaller, higher speed devices, materials for back-end of line processes are needed to reduce resistance-capacitance time delay in next generation integrated circuits. Hence, process integration now involves new thin film materials such as low k, copper and other novel materials.

Several materials are prone to delaminate or exhibit detrimental physical and material changes upon heating and cooling. Problems are compounded by the requirements of multiple layers of coatings or thin films. Consequently manufacturers are requiring greater adhesion specifications. Failing to meet these greater specifications can preclude the manufacturer's product from entering the marketplace. Thus, data on the mechanical reliability of these new materials is critical. However, since such data is not available, sufficient test data needs to be developed to aid in the prediction of a product's use limit or lifetime and reliability.

Adhesive failure can be predicted when applied energy exceeds a critical fracture property of a union. The demand in designing and measuring adhesion is to establish the characteristics of both the applied energies and the critical performance properties. Performance properties vary with a myriad of processing and environmental conditions, hence, any test developed to measure these properties must be capable of simulating the same processing conditions.

Of great concern is adhesive failure due to large thermal stresses developing during processing. To be able to predict the behavior of a design, failure data must be available to compare to known stress fields.

Early attempts to measure adhesion included the use of the tape test and a method of abrasion. The tape method consisted of pressing a piece of adhesive tape to the film. The tape is then pulled off the film either leaving the film intact, removed in whole or in part, or remaining on the substrate. This method is qualitative only, and if the film remains on the substrate, it provides no quantitative data as to the magnitude of the adhesion forces. Failure of the tape test implies that the film is unsuitable for device fabrication.

The abrasion or scratch test method results depend on the film hardness as well as on its adhesion. All of these conventional tests for adhesion are qualitative at best and do not accurately model the fracture mechanism.

The modified Edge Liftoff Test has been developed and applied to testing multilevel coatings on a rigid substrate. This test is applicable to testing the adhesiveness of multilayers of microelectronic structures in that it allows testing of samples constructed with standard back-end of line processes.

A thick coating of epoxy is applied to a multilayer device. Failure of the adhesive forces is caused by the stored strain energy in the thick epoxy layer exceeding the critical adhesion energy of the weakest component interface as the test sample is cooled. Advantages of this type of testing are simplicity and resultant true fracture energies of the system. Reliability of the device can be quickly assessed by comparing the measured fracture energies to the calculated applied fracture energies from finite element analyses. However, this system generally requires a human observer to continually peer through glass plates to monitor delamination of the films.

In view of the above, what is needed is a modified edge lift test system capable of providing consistent data of the adhesion characteristics of films and coatings. The system should be capable of sealed automatic temperature processing, including computer controlled delamination detection and temperature control.

SUMMARY OF THE INVENTION

To address current industry needs, the invention offers a modified edge lift test system which includes a sealed automatic temperature processing type chamber that operates in a computer controlled heating and cooling mode, and a computer processor with delamination detecting software. The invention's ability to provide consistent data of the adhesion characteristics of old and new films and coatings can provide valuable processing data to the industry and speed up the manufacturing process. This invention is particularly applicable to industries such as semiconductor manufacturing where the search for new thin film materials and coatings is ongoing.

The invention provides for an improved system for quantitative and qualitative testing of the adhesion characteristics of thin film materials and coatings during thermal processing. In one embodiment, an apparatus of the present invention includes an atmosphere sealable chamber set within a metal housing. An optical window made of a transparent temperature stable material such as Plexiglas, glass or quartz mounted in a wall of the chamber to view the samples being tested. A sample tray holder, capable of holding multiple samples, inserted though a side wall of the chamber and lockable into position. A camera is mounted on top of the optical window to replace a human observer in monitoring the testing process. Lighting is mounted adjacent to the improved optical window to provide a sufficient amount of light to illuminate the samples being tested for observation and recordation. A computer processor, with image processing software, is connected to the testing apparatus and the camera for collection and analysis of temperature and visual data gathered during the testing process.

In another embodiment, a sample tray is inserted into the chamber through a slot in the wall of the chamber and sealed with clamps. In yet a further embodiment, a single viewing window made of a solid temperature stable material is used to address the problems of shadows, ghost images, double reflection, and frost.

In one aspect of the invention, two lamps, one mounted on two different sides of the viewing window are utilized to provide a constant and sufficient amount of light for optical viewing and recording by a camera mounted on top of the viewing window. The lamps provide a ghost free, shadow free, viewing and recording of sample images.

Advantageously, the present invention provides more efficient thermal transfer by using an improved heat exchanger where the heating/cooling surface has raised posts. Moreover, the present invention uses an automated gas and liquid nitrogen mixer assembly. Through the use of gages or reducers and valve configuration, the computer controls the opening or closing of valves to set the flow of gas and liquid nitrogen into proper ratios prior to introduction into the chamber for either a specified temperature range or time period.

Another advantage of the present invention is the use of a digital camera to record an image change in the place of a human operator and computer imaging software which captures and records debonding of samples and the temperatures at which debonding occurs and then calculates the debonding energies. In addition, the present invention provides complete automation and control of the entire process by computer, from heating through cooling and calculation of debonding energies, with graphing of data in a visual chart for the user.

BRIEF DESCRIPTION OF THE DRAWINGS

The invention together with further advantages thereof, may best be understood by reference to the following description taken in conjunction with the accompanying drawings in which.

DETAILED DESCRIPTION OF THE INVENTION

Figure 1:
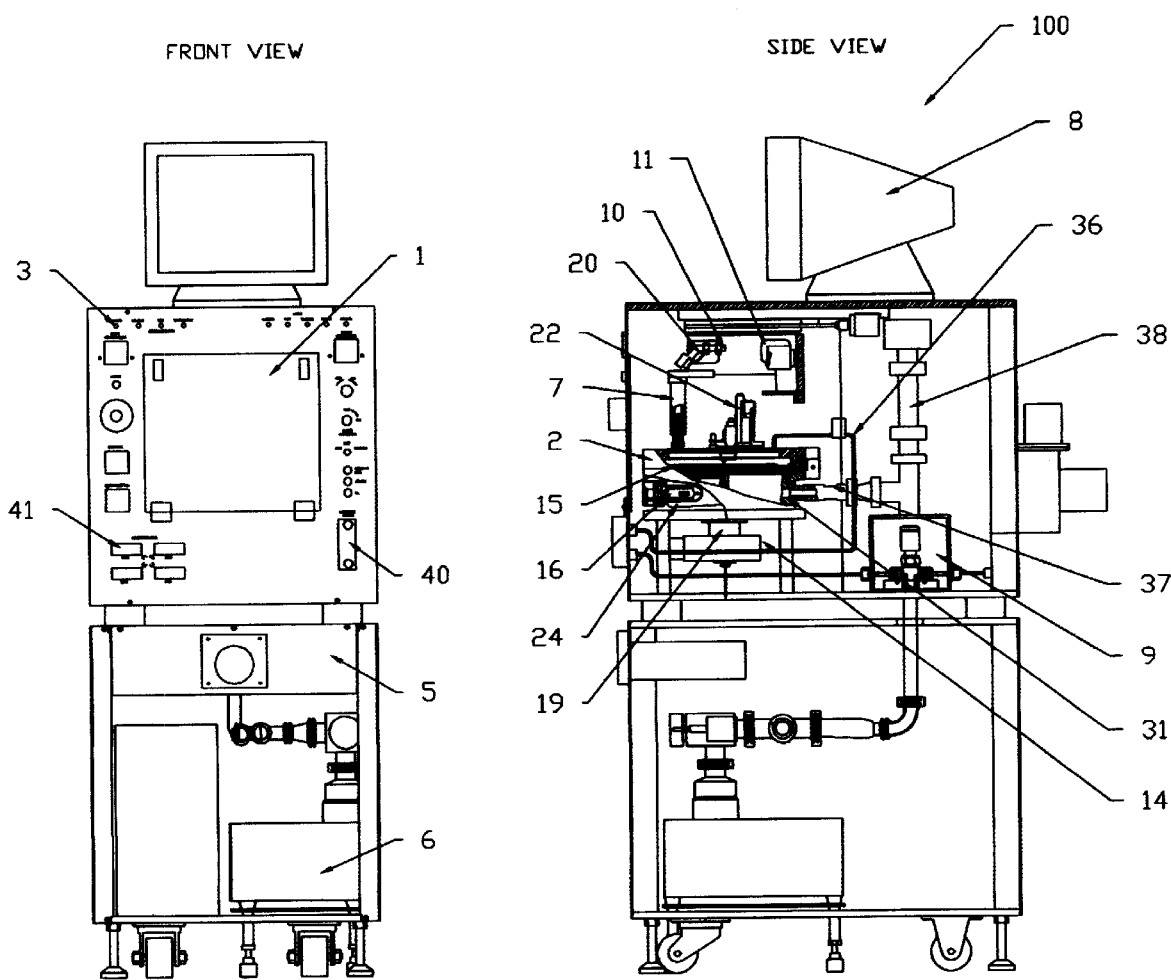
FIG. 1 is a pictorial view of an apparatus for testing the adhesion characteristics of thin film materials and coatings during thermal processing in accordance with one embodiment of the present invention which includes the testing chamber, a temperature control unit and a computer processor.
Figure 2:
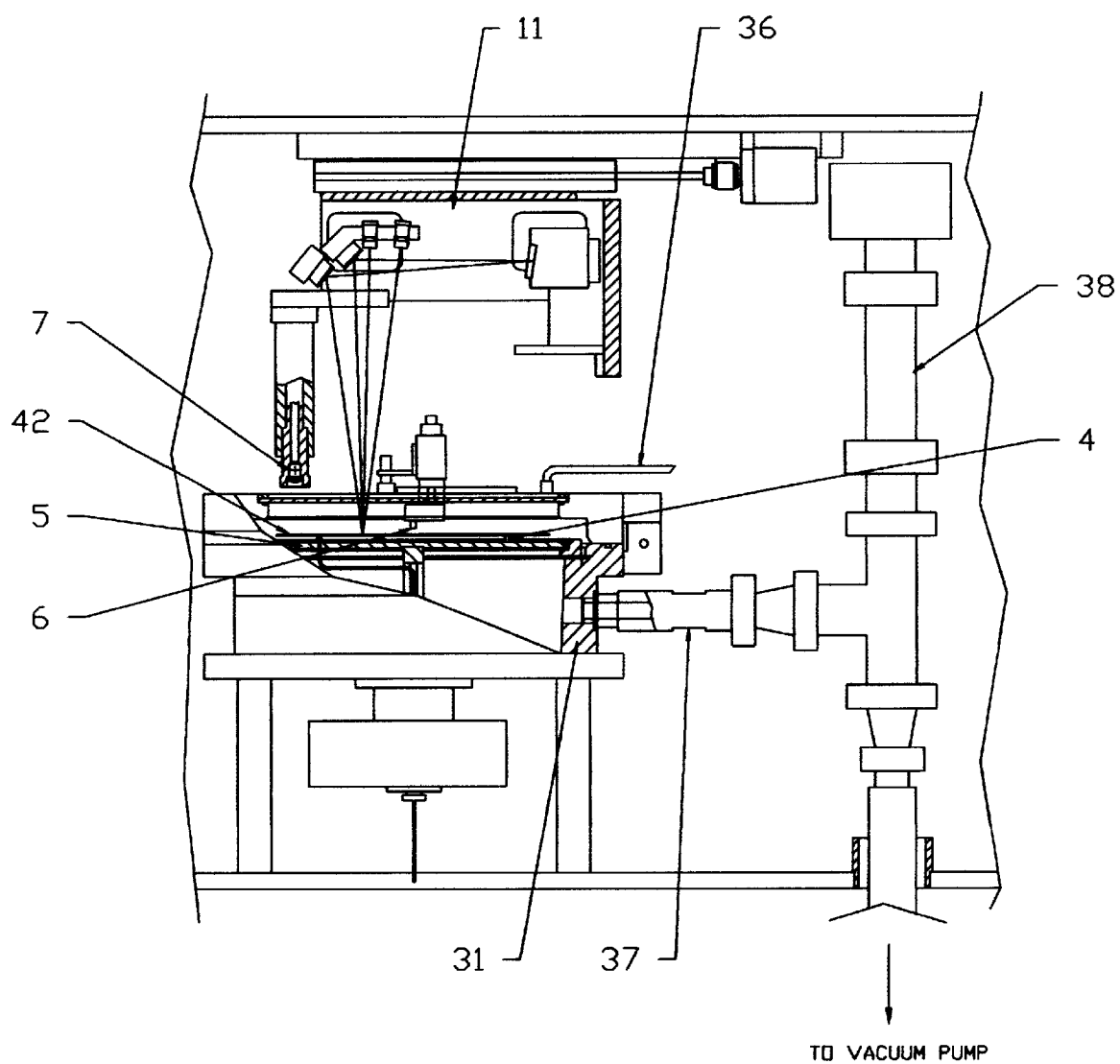
FIG. 2 is a pictorial view of the sample tray in accordance with an embodiment of the present invention.
Figure 3A:
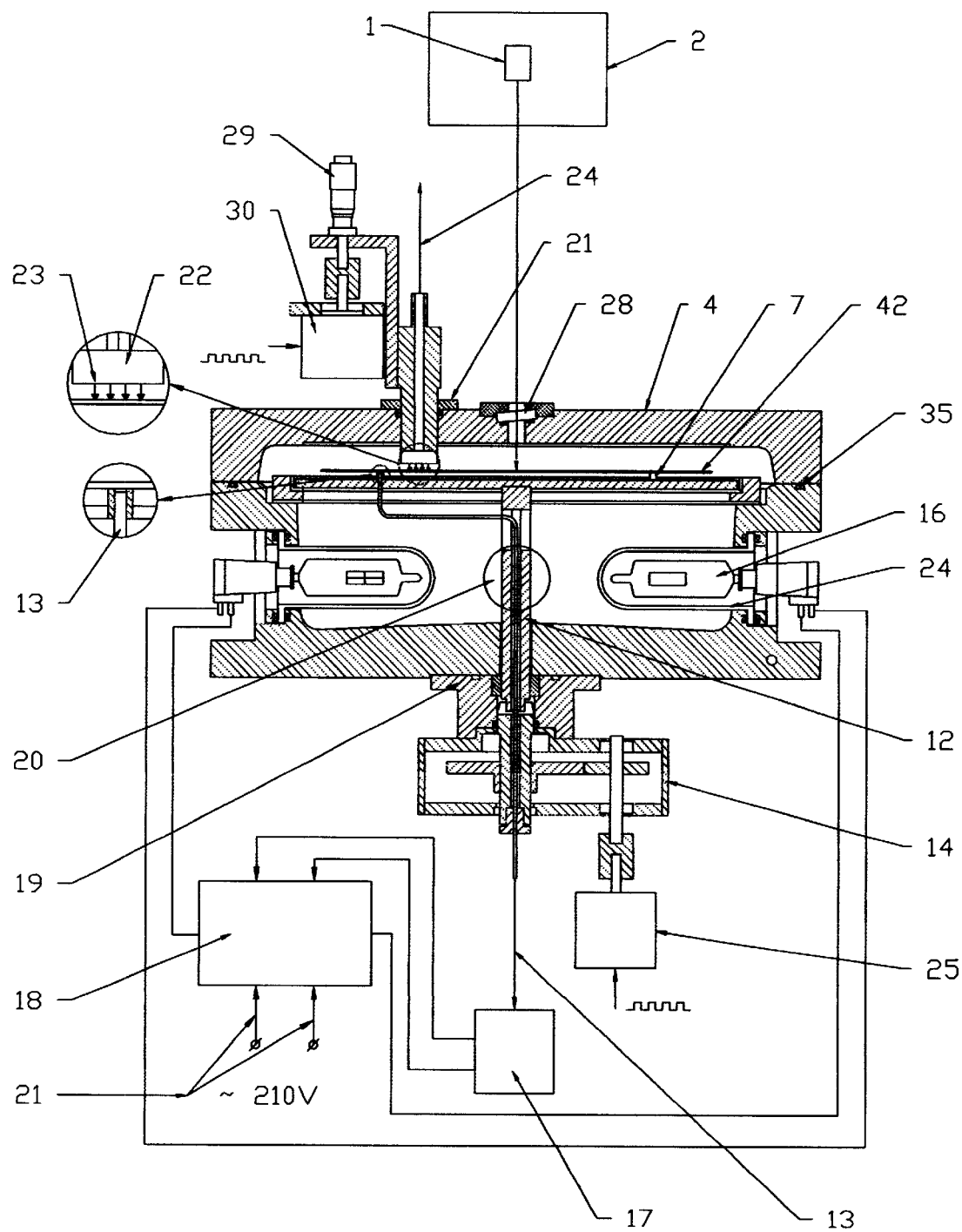
FIG. 3 is a pictorial view of the optical window in accordance with another embodiment of the present invention.
Figure 3B:
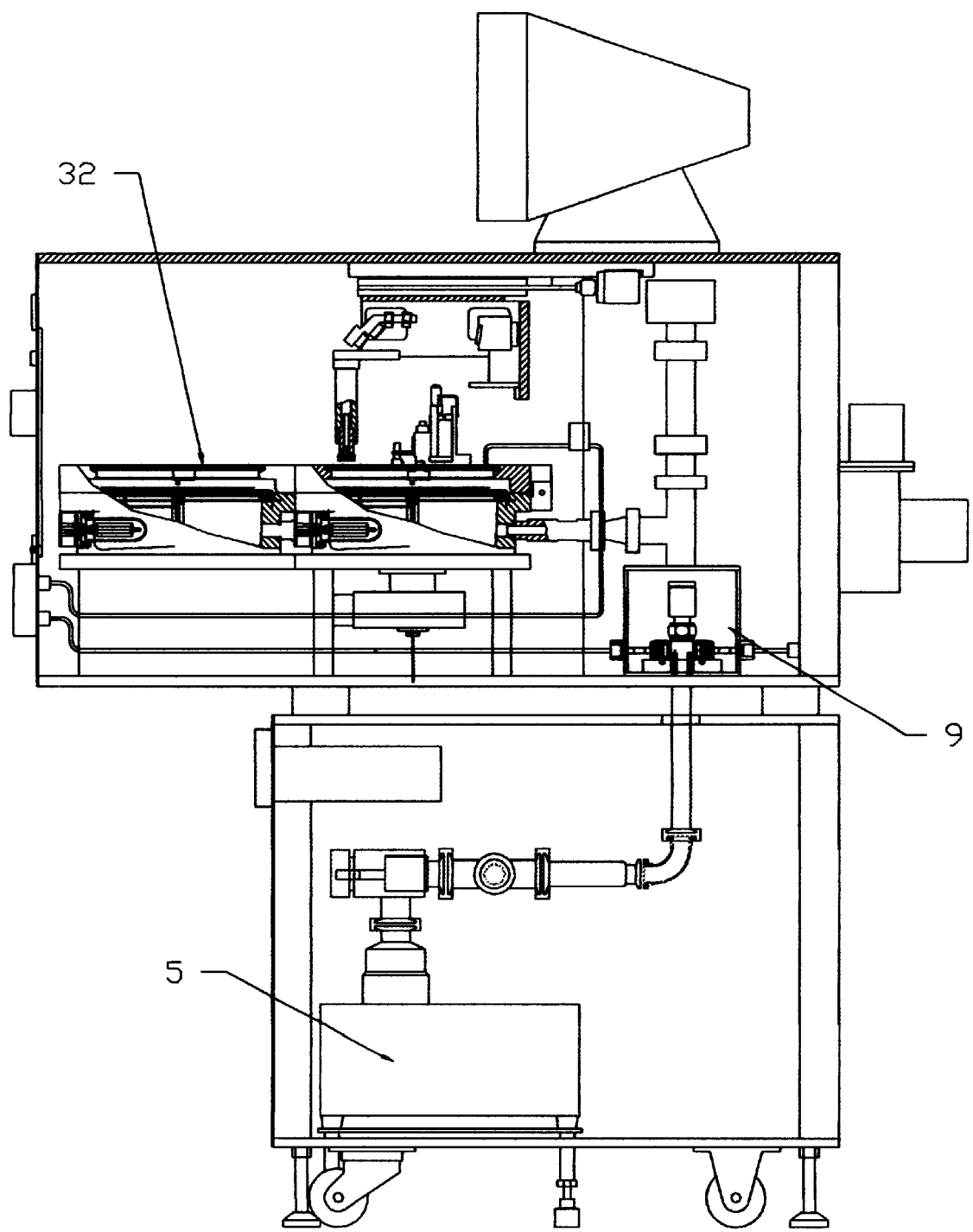
Figure 4:
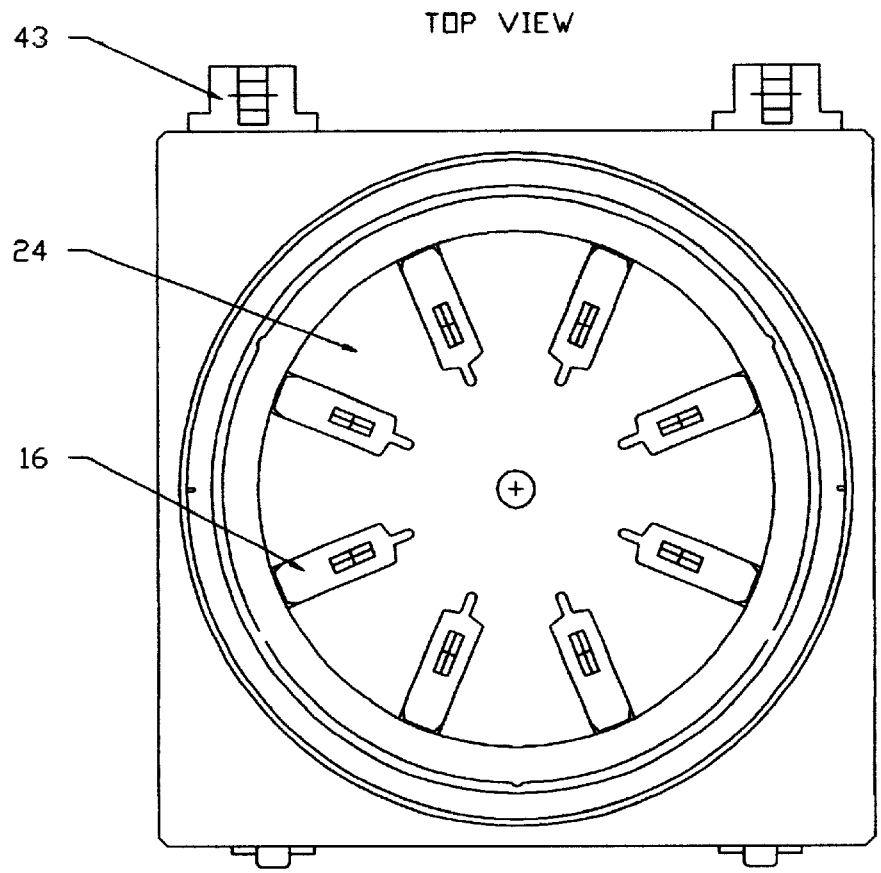
FIG. 4 is a pictorial view of the mounted lighting in accordance with an embodiment of the present invention.
Figure 4:
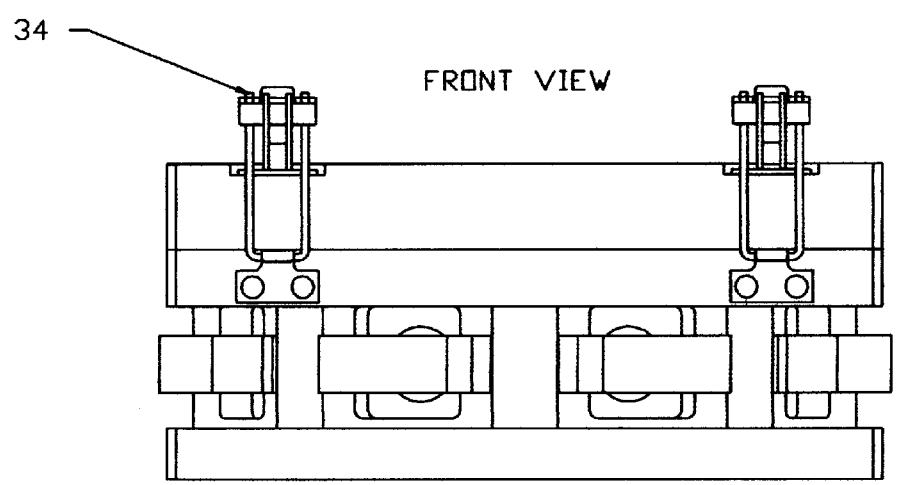
Figure 5:
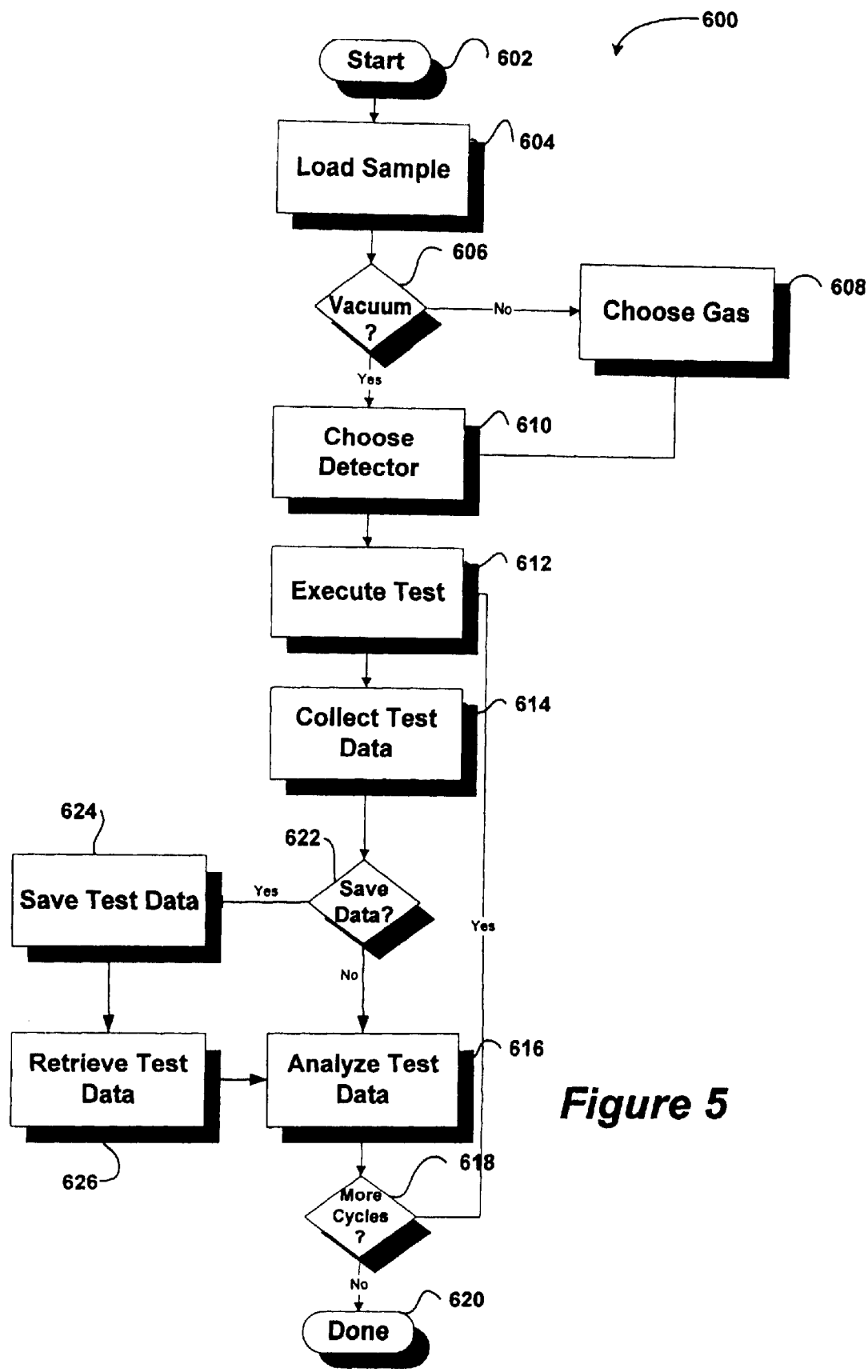
FIG. 5 is a pictorial view of the heat exchanger in accordance with an embodiment of the present invention.
Figure 6:
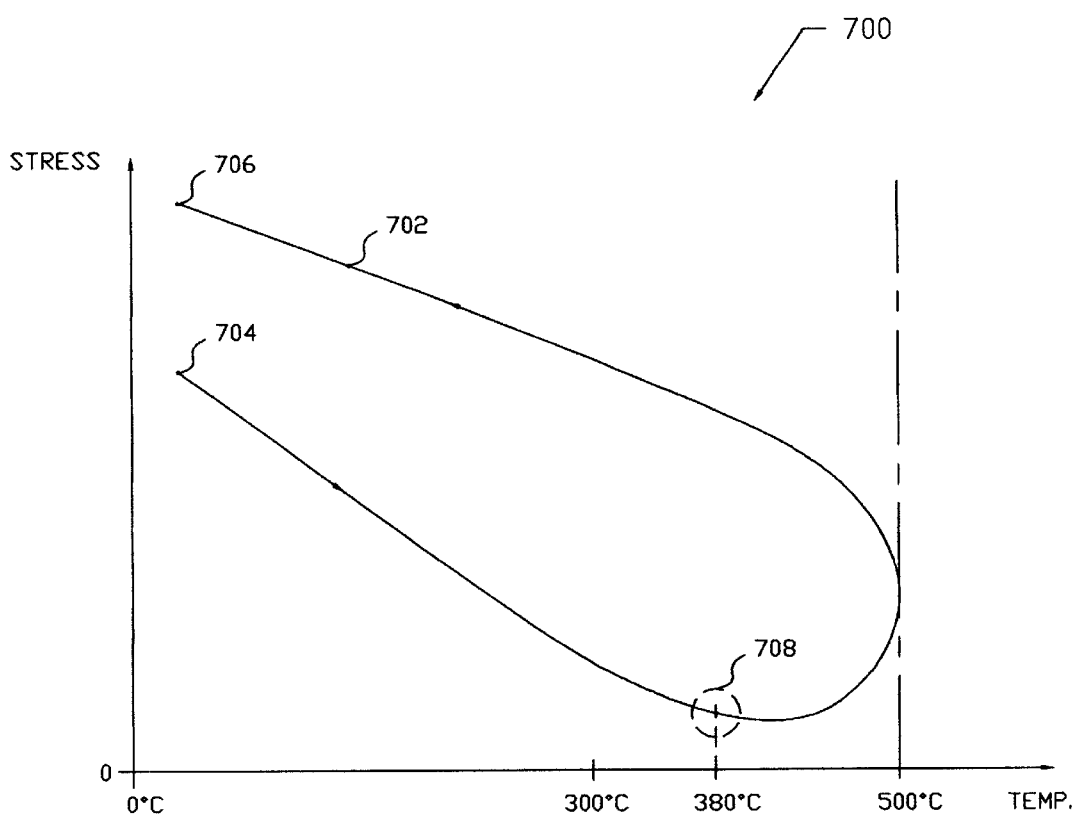
FIG. 6 is a pictorial view of the gas and liquid nitrogen mixer assembly in accordance with an embodiment of the present invention.
Figure 7:
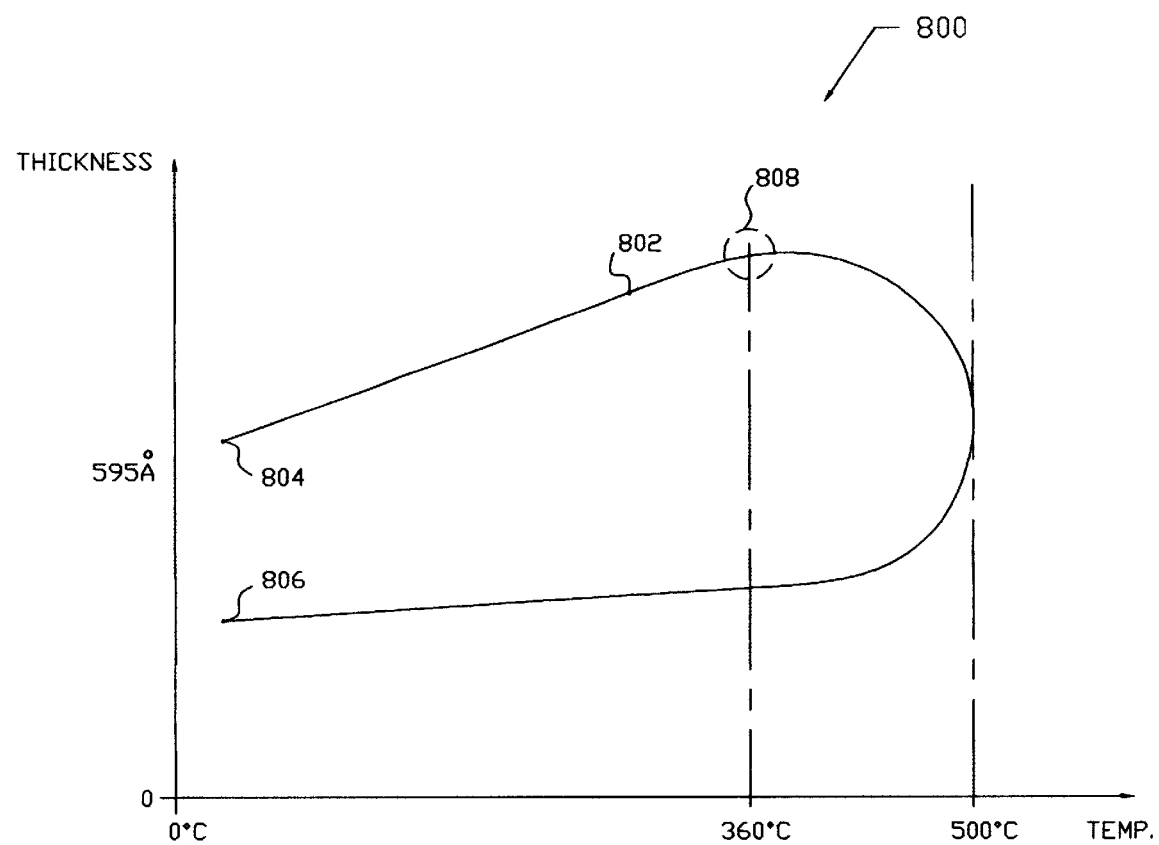
FIG. 7 is a pictorial view of the gas and liquid nitrogen mixer and a gas flow gauge in accordance with an embodiment of the present invention.

An invention is disclosed for an improved system for quantitative and qualitative testing of adhesion characteristics of thin film materials and coatings during thermal processing. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

FIGS. 1–7 illustrate an apparatus of the preferred embodiment of an improved system for quantitative and qualitative testing of the adhesion characteristics of thin film materials and coatings during thermal processing.

The invention includes a housing; an atmosphere sealable chamber 6 capable of achieving multiple temperatures; an improved optical window 3 made of a transparent temperature stable material such as Plexiglas, glass or quartz mounted in a wall of the chamber, a sample tray holder 4 inserted though a wall of the chamber and lockable into position, a heat exchanger/mixer 12, a thermocouple 1, a camera 9 and lighting 2 mounted adjacent to the improved optical window to monitor the samples during testing, mixing assembly 8, control valves 17 and gages 16 for mixing gas and liquid coolant, a temperature control unit 5 and a computer processor 7, with image processing software, connected to the testing machine and camera for collection and analysis of temperature and visual data.

Additionally the invention can be fitted with an acoustic and/or a laser detector sensing devices for gathering temperature and delamination data.

In practice, prior to testing, a sample silicon wafer is first measured for thickness with a micrometer. Next epoxy is placed on the wafer to act as a backing layer over the thin film so that the point of delamination can be more easily observed during testing. To ensure good adhesion between the epoxy and the test layer, an epoxy, chosen for its good wetting, adhesion, and to provide sufficient energy to cause delamination, is applied with an epoxy applicator to the wafer, to a measurable thickness of approximately 100 microns. The actual thickness of the thin film is so proportionately thinner than the thickness of the epoxy as to be negligible in terms of the film's thickness measurement compared to the epoxy thickness.

The wafer with an epoxy coating is then cured in an oven for about an hour.

The cured epoxy coated silicon wafer sample to be tested is first divided into rectangular portions to obtain edges that are 90 degrees to the interface. Each square sample is measured with a micrometer at each of its four corners for thickness and recorded. The rectangular portions are placed on the sample tray 4 in the sample spots 13.

The invention has a sample tray which is inserted into the chamber through a slot in the wall of the chamber and sealed with clamps 63. The sample tray has convection accelerator holes 14 placed around the sample spots 13 to more efficiently effect cooling. The sample tray is then placed in the testing chamber 6.

A temperature control unit 5 is used to control heating and cooling by controlling the coolant circulating through the heat exchanger/mixer 12. The samples may be heated to an elevated temperature of about 100 degrees Centigrade by the heat exchanger/mixer 12 in the chamber. An advantage of the invention is the improvement in the heat exchanger/mixer 12 where the heating/cooling surface has raised posts 10 for more efficient thermal transfer.

Chamber temperature and thermal cycling is monitored by a thermocouple, located near or contacting a sample or sample tray, and is controlled by an electrical temperature control unit 5. Samples are electrically warmed by the heat exchanger upper body plate 18 to a selected temperature. Samples are cooled by the heat exchanger/mixer 12 by the introduction of a cooling gas and liquid nitrogen mixture, from the mixer assembly 8, mounted below the sample tray, which is fed by gas lines from a cylinder of liquid nitrogen, until fracture is observed.

The heat exchanger/mixer 12 is mounted below the sample tray 4 to provide a heating and cooling source for varying the temperature of the samples during thermal cycling. The heat exchanger/mixer is electrically wired for heating by electrical resistor 15. Heating and cooling is facilitated through the heat exchanger/mixer 12 by the raised posts 10 inserted in the heat exchanger upper body plate 18.

The heat exchanger/mixer 12 consists of a heating element 15 for heating samples to an elevated temperature, and a mixing chamber where gas and liquid nitrogen are mixed by the gas/fluid mixers to cool the sample until fracture is observed. The mixture of gaseous and liquid nitrogen is controlled by valves 17 which control the amount of coolant into the gas/liquid nitrogen mixer 11 which permits efficient controlled cooling of the testing chamber.

An advantage of the invention is the automated gas and liquid nitrogen mixer assembly 8. Through the use of gages 16 or reducers and valve 17 configuration, the computer controls the opening or closing of valves to set the flow of gas and liquid nitrogen into proper ratios prior to introduction into the chamber for either a specified temperature range or time period.

The amount of cooling mixture of gas and liquid nitrogen comes from the mixer assembly 8, mounted below the sample tray, which is fed by gas lines from a cylinder of liquid nitrogen, and is controlled by valves 17 and gages 16 before entry into the heat exchanger/mixer 12. The mixer assembly 8 combines liquid and gas nitrogen into the proper ratios outside of the chamber and is passed into the heat exchanger/mixer inside of the chamber through the predistributors 11 inserted in the heat exchanger/mixer lower body plate 19.

Improved optical viewing is accomplished through a window 3 on top of the chamber made of a one-piece solid transparent temperature stable material such as quartz, glass, Plexiglas or suitable transparent material. The invention has resolved the problems of shadows, ghost images, double reflection and frost problems caused by multiple glass paned windows, by utilizing a single viewing window made of a solid temperature stable material. The solid window removed the additional burden of passing warm nitrogen gas over the multiple glass paned window to remove frost. The solid window removed the double reflection and ghost images caused by the use of multiple plates of glass. A clear, transparent optical window 3 is mounted in the chamber wall above the sample tray for optical scanning by camera 9 or human eye.

The invention has lighting consisting of two lamps 2, one mounted on two different sides of the viewing window to provide a constant and sufficient amount of light for optical viewing and recording by a camera 9 mounted on top of the viewing window. The camera removes the requirement of a human observer continually peering through the window to monitor debonding.

The lamps provide a ghost free, shadow free, viewing and recording of sample images. The lamps 2 for illuminating the sample tray are mounted next to the camera. A thermal couple 1 is mounted within the chamber to measure temperature. The camera takes snapshots of the sample tray at each one degree drop in temperature. As the samples cool, the camera records the moment of fracture of the film from the substrate and the computer processor captures the event with its image processing software and records the temperature at the moment of debonding.

An advantage of the invention is the use of a digital camera to record changes in place of a human operator and computer imaging software which captures and records debonding of samples and the temperatures at which debonding occurs and then calculates the debonding energies. Information collected from the temperature control unit 5 and camera 9 is collected and analyzed by the computer processor 7 to provide an analysis of the adhesion characteristics of each sample being tested during the thermal cycling.

A computer 7 and camera system with image imaging software is used to control and record the entire heating/ cooling process either over a specified time period or over a specified temperature range, at one degree temperature increments until the moment of fracture or delamination of each sample, as well as recording the temperature at the moment of fracture or delamination 64.

Figure 8:
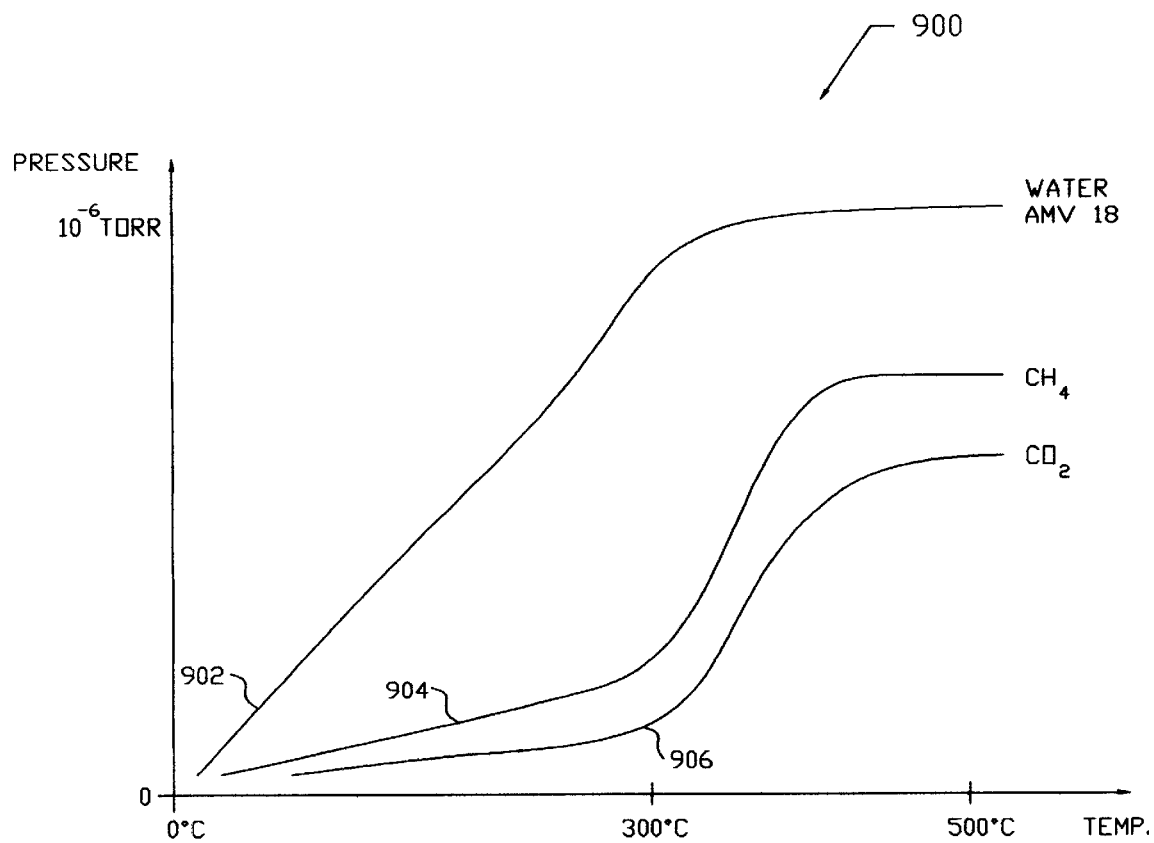
FIG. 8 is a flow chart showing a method for measuring the adhesion characteristics of thin film materials and coatings during thermal processing according to one embodiment of the invention.

FIG. 8 is a flow chart showing a method 900 for measuring the adhesion characteristics of thin film materials and coatings during thermal processing according to one embodiment of the invention. Sample preparation 901 begins with cleaning and measuring of samples for thickness, the application of epoxy, curing the epoxy, portioning the samples and measuring the portioned epoxy coated samples. Sample thickness data is stored. The samples are loaded 902. The user decides the setup parameters 903 and starts the experiment 904.

Data is collected 905 and a decision is made to either save the data to storage 906 or process and analyze 908 the data. At the completion of data analysis a report 909 is generated with the test results.

Figure 9:
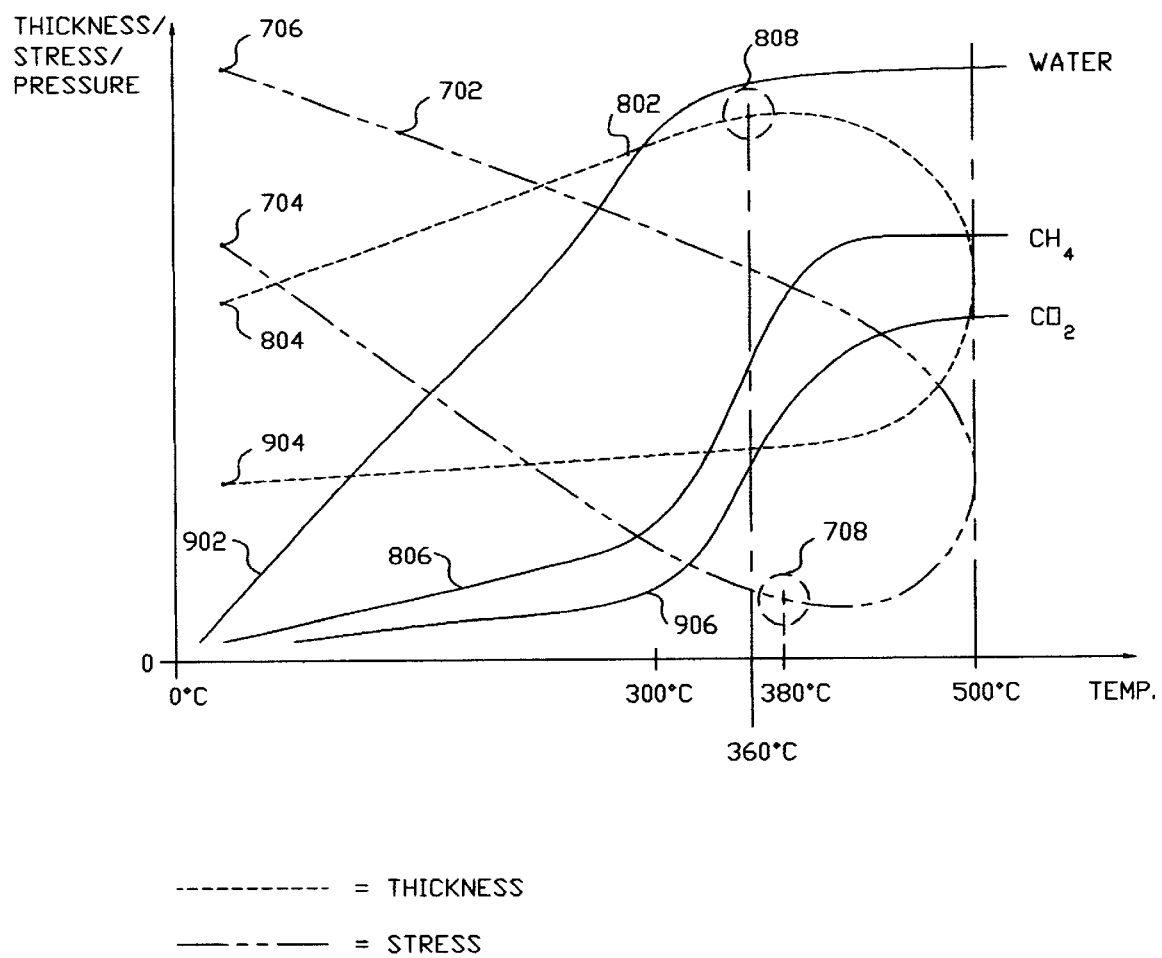
FIG. 9 is a flowchart showing a method for data collection in accordance with an embodiment of the present invention.

FIG. 9 is a flowchart showing the steps of data collection as illustrated in FIG. 8. Data collections begins with collecting images from the image capturing device 910. Next temperature and time data from sensors is collected 911 and saved to storage 912. A decision is made whether to continue 913 the experiment to conclusion with the saved data or repeat the data collection process. Data is captured at each one degree increment of temperature drop.

Figure 10:
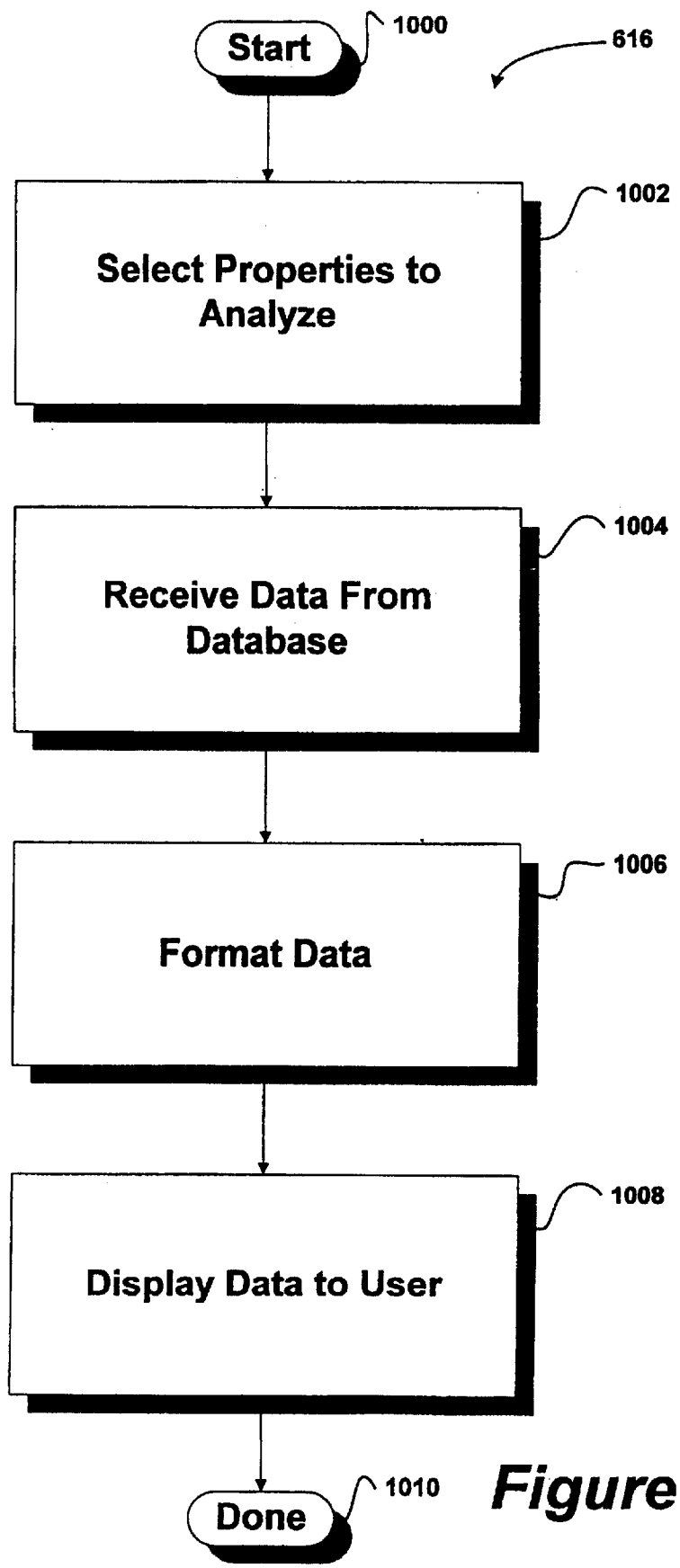
FIG. 10 is a flow chart showing a method for processing and analyzing data from tests performed on samples in accordance with an embodiment of the present invention.

FIG. 10 is a flow chart showing a method for processing and analyzing the data from tests performed on samples as illustrated in FIG. 8. In data processing, a first image 914 of the samples is collected at a temperature T1 and a second image 915 is collected at T2. Both images are compared using comparison filters 916 resulting in a third image 917. Using morphological filters 918 on the third image results in a fourth image 919.

Data analysis begins with feature extraction filters 920 applied to the fourth image resulting in a fifth image 921. Test results are then calculated and a decision is made whether to process more images 923 or by repeating the data processing process again, or finish with a report 909.

Figure 11:
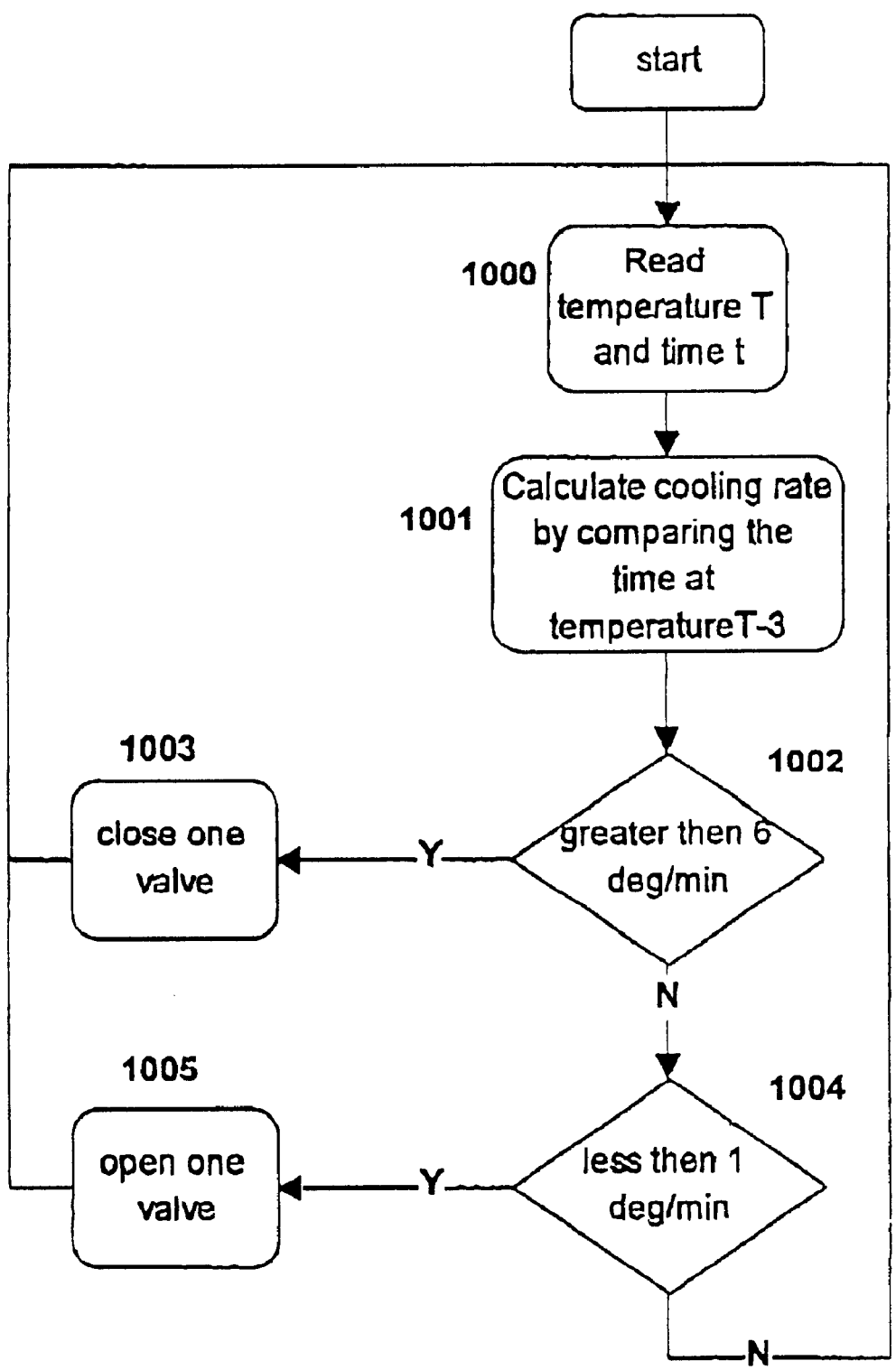
FIG. 11 is a flow chart showing a method for temperature control during the testing of samples in accordance with an embodiment of the present invention.
Figure 1:
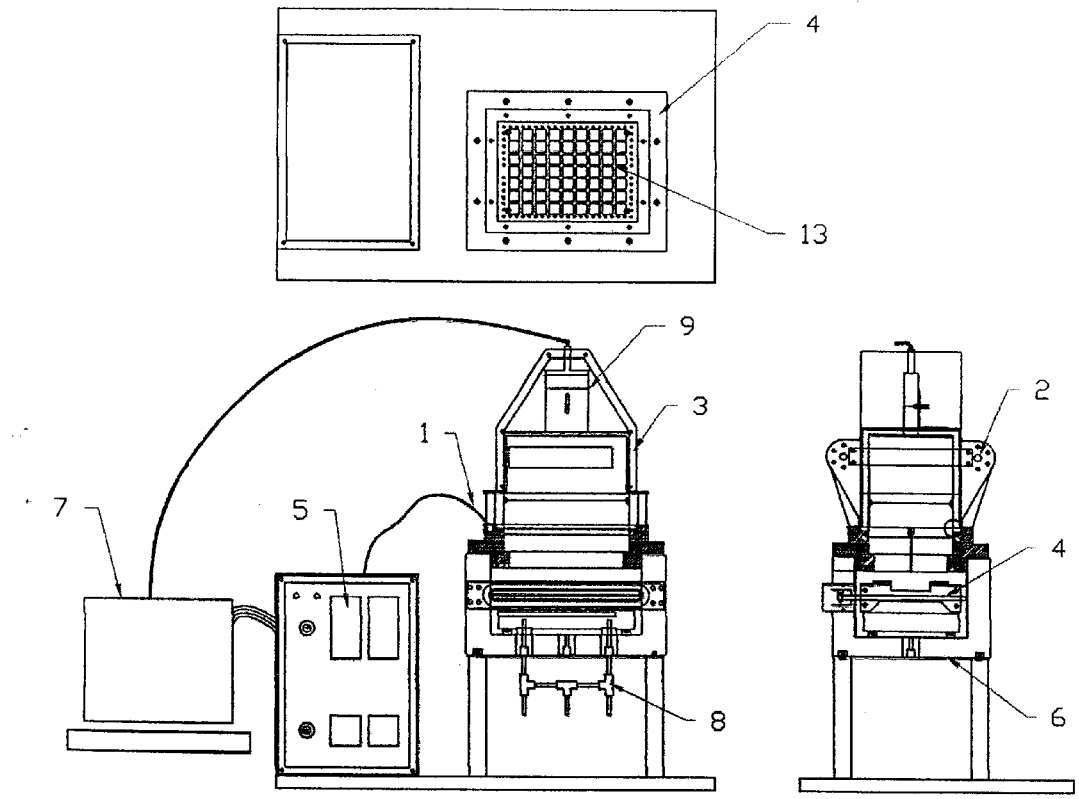
Figure 2:
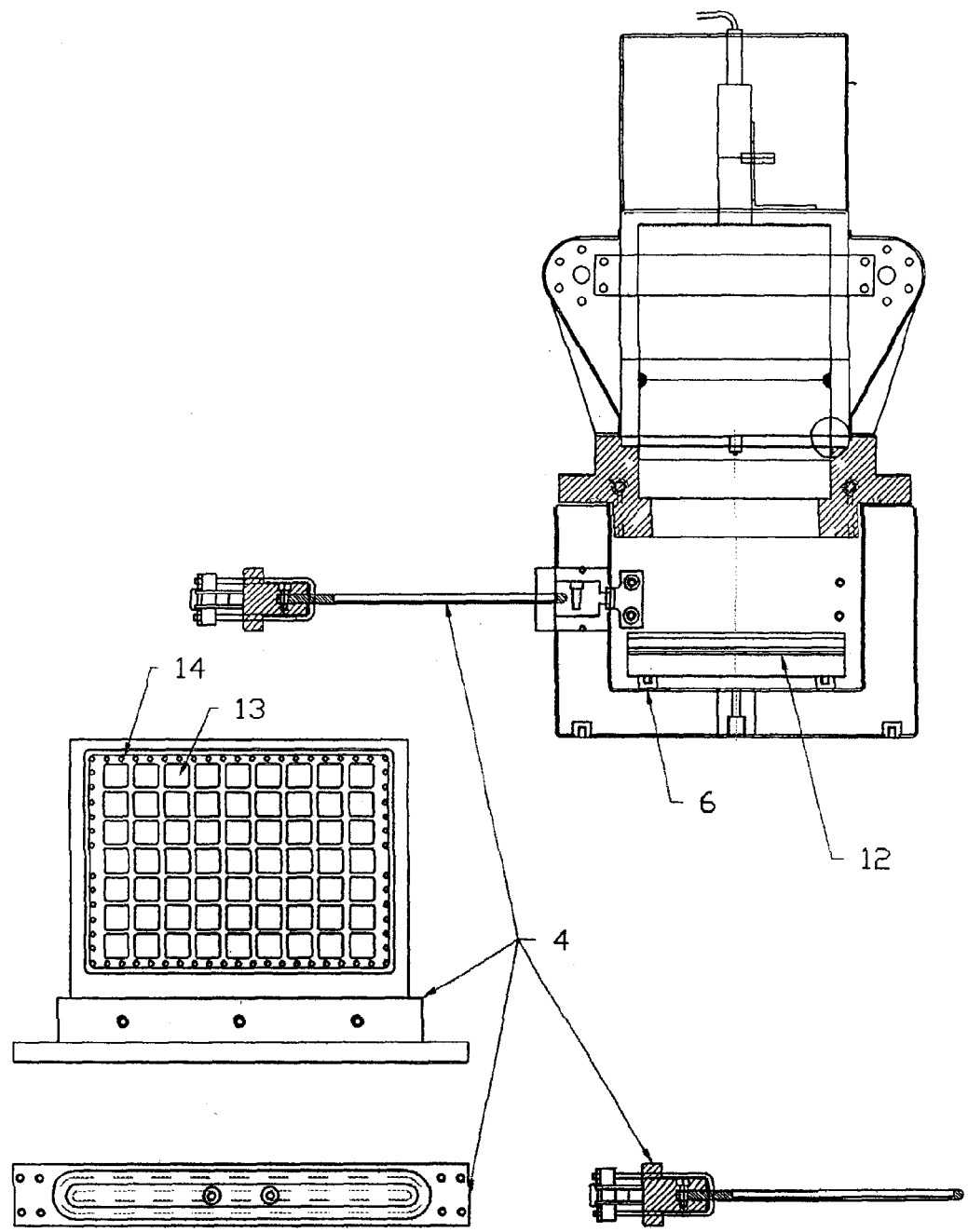
Figure 3:
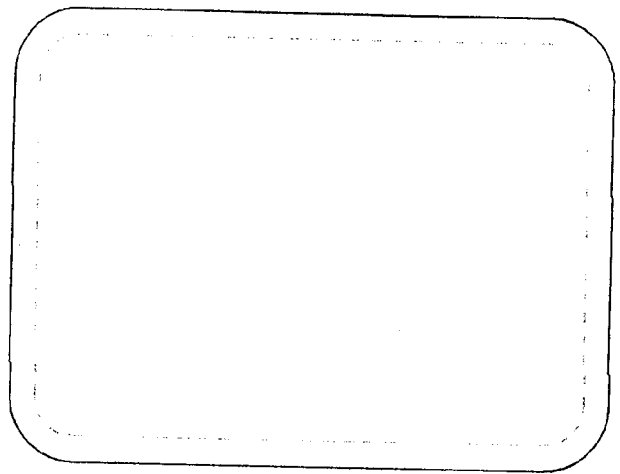
Figure 3:
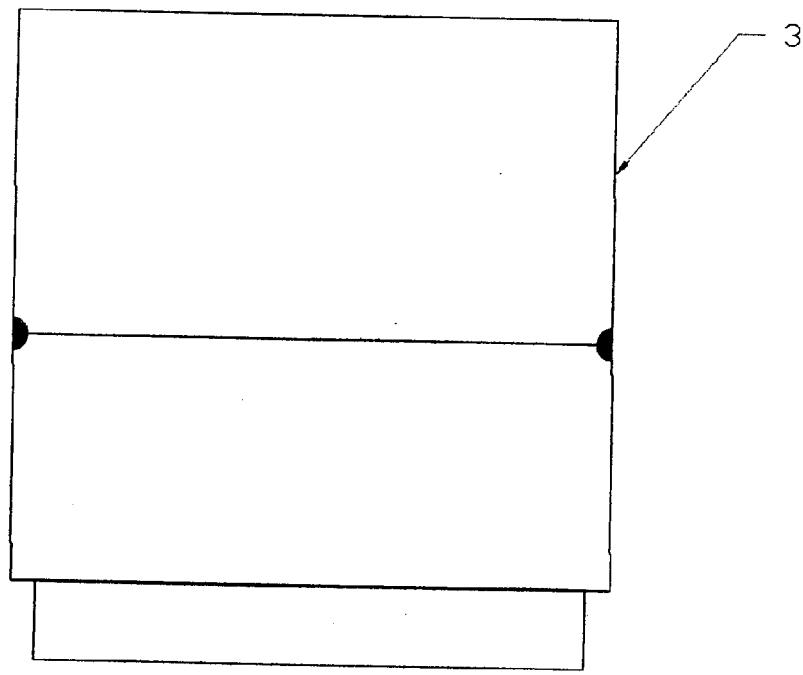
Figure 4:
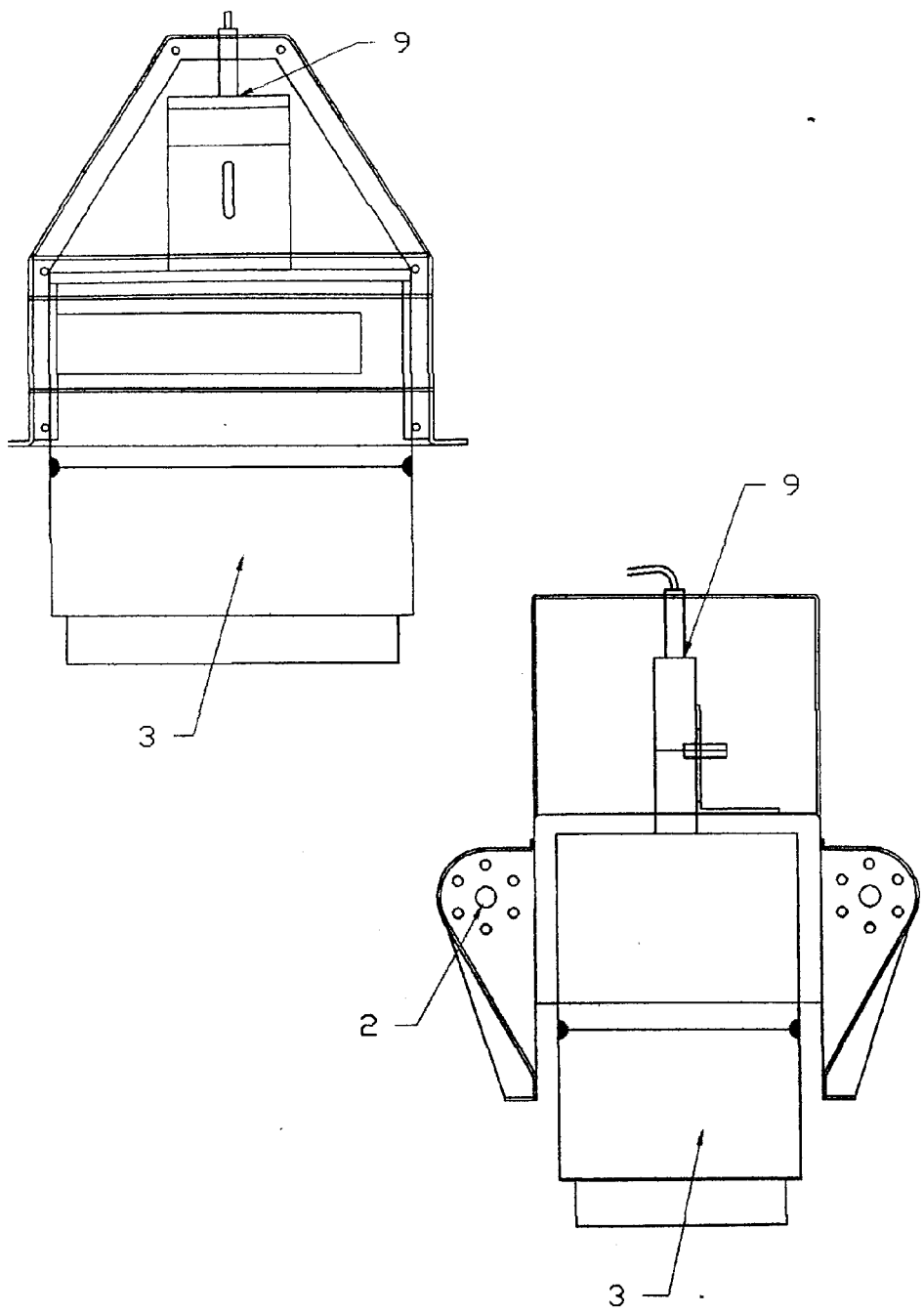
Figure 5:
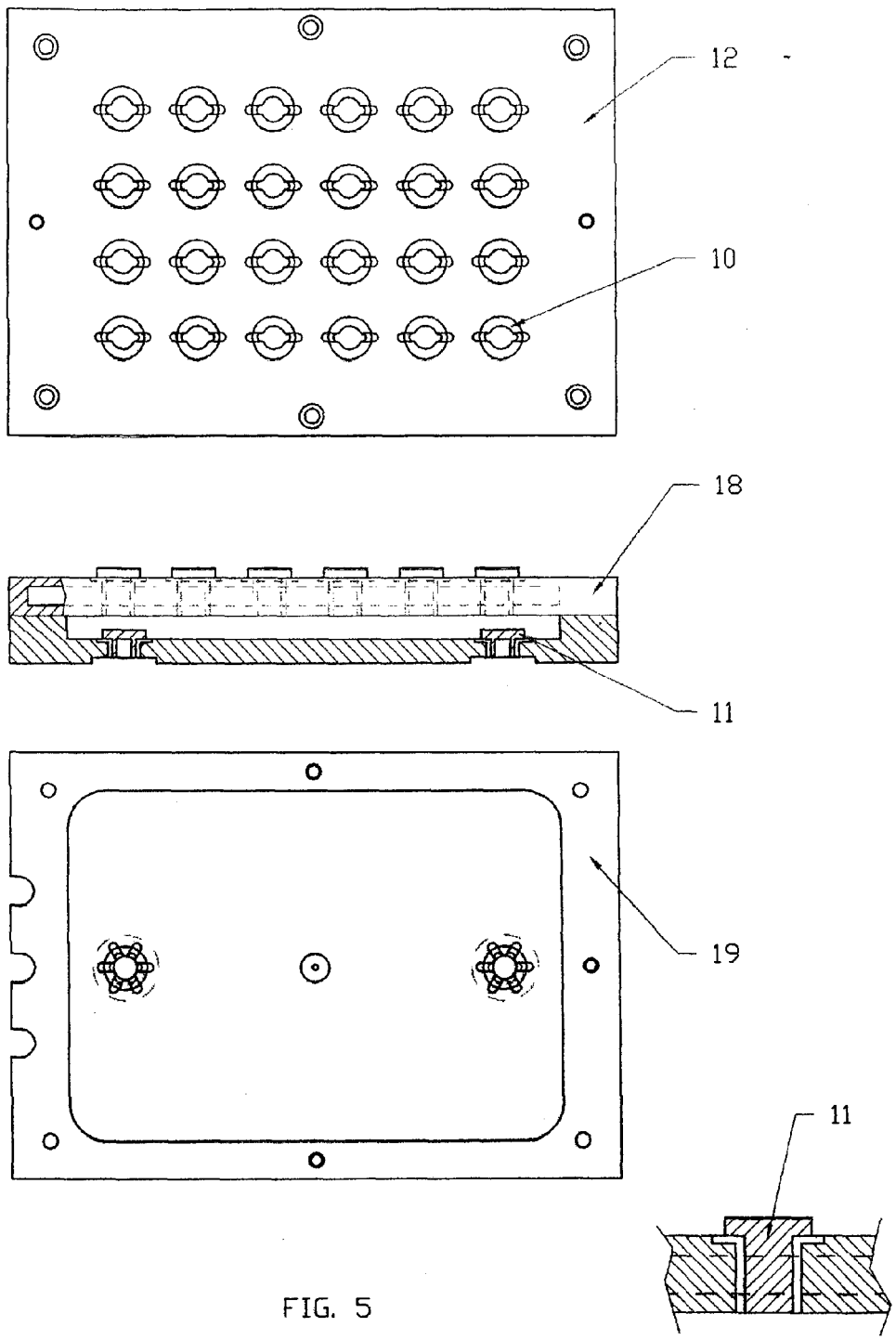
Figure 6:
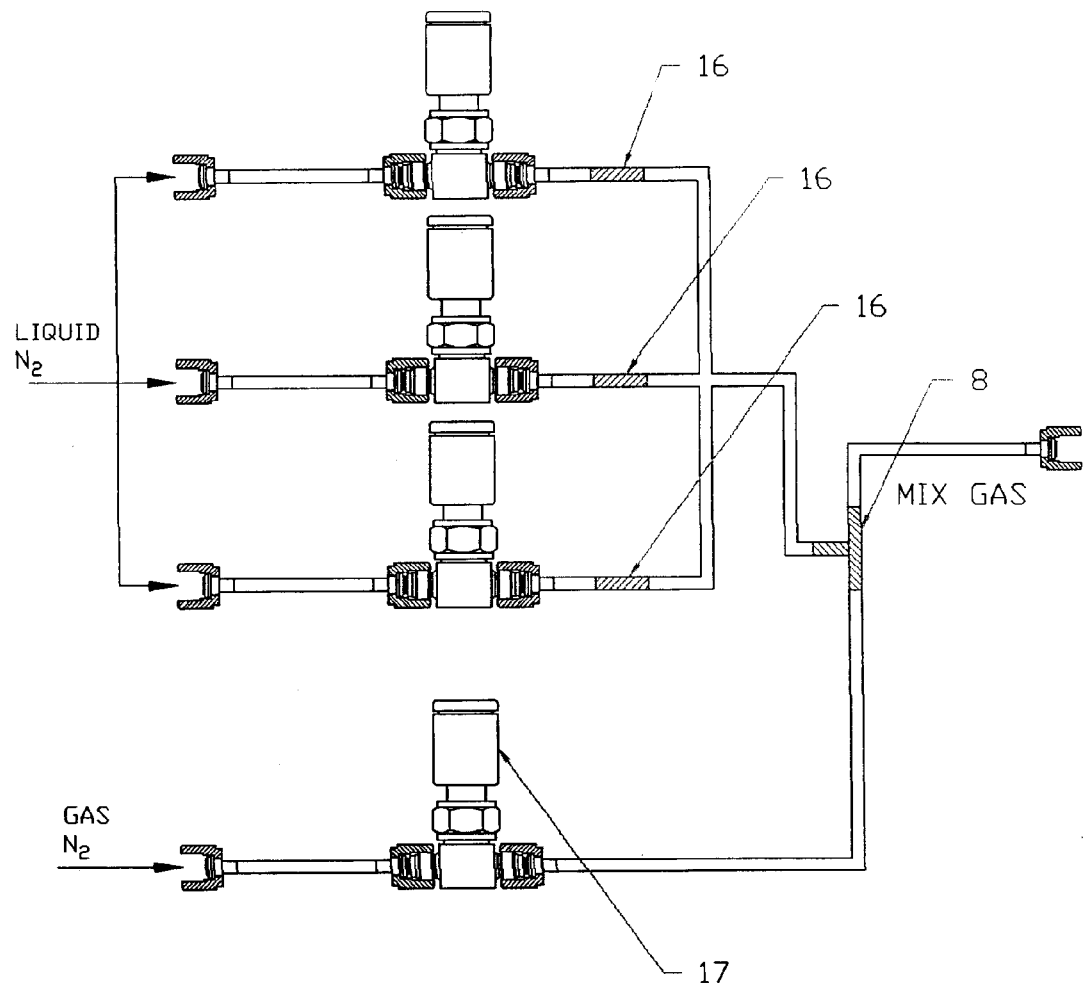
Figure 7:
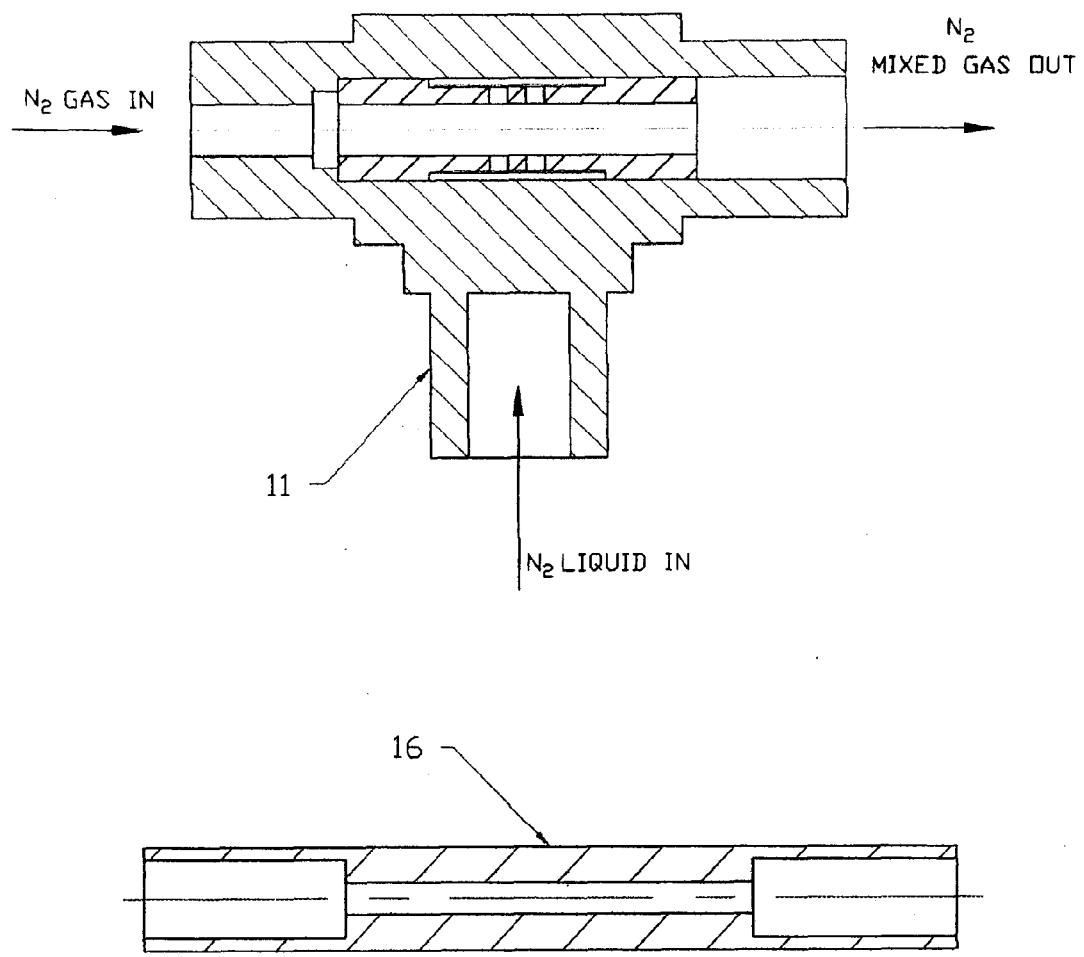
Figure 8:
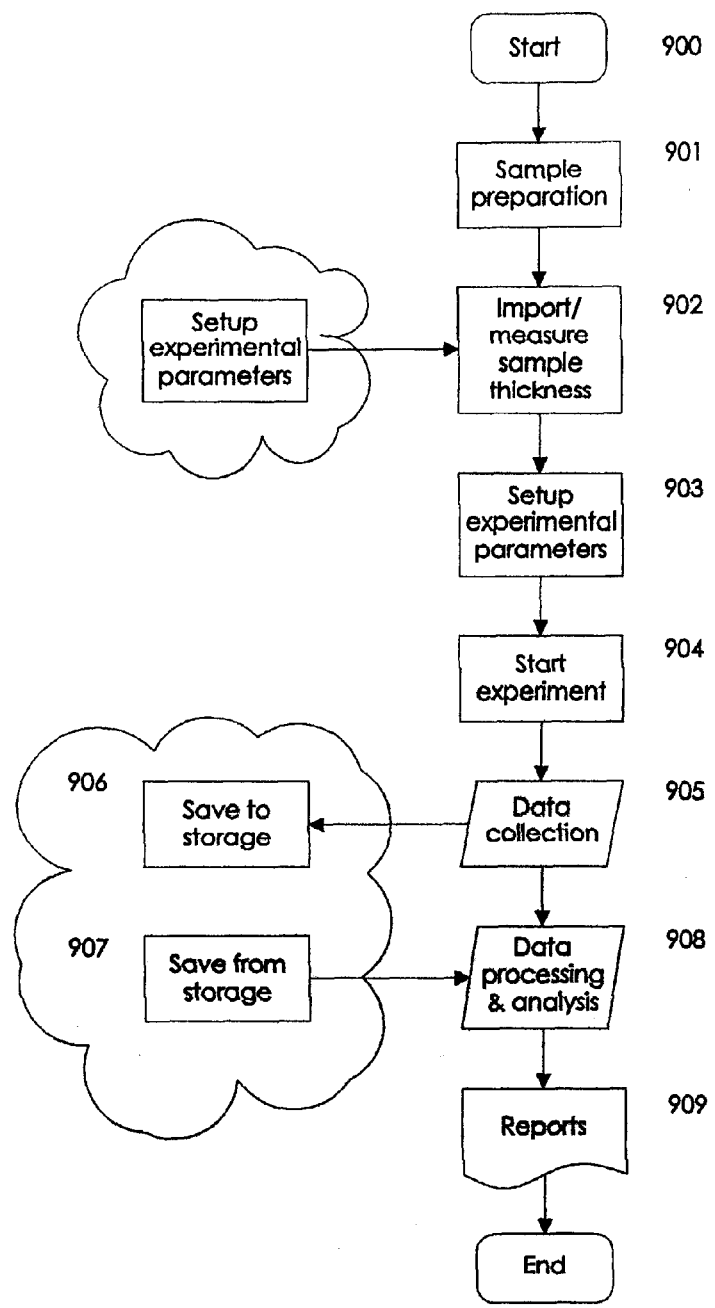
Figure 9:
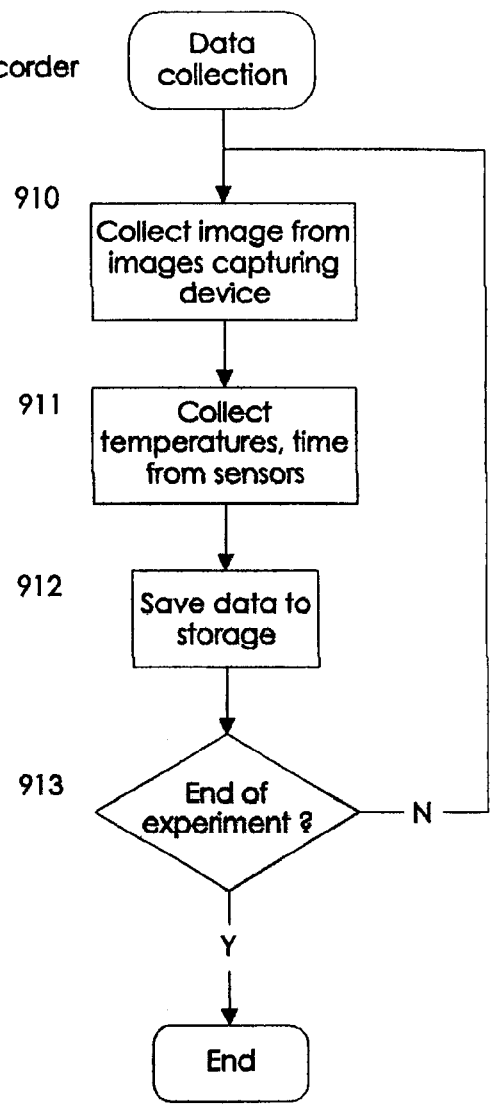
Figure 10:
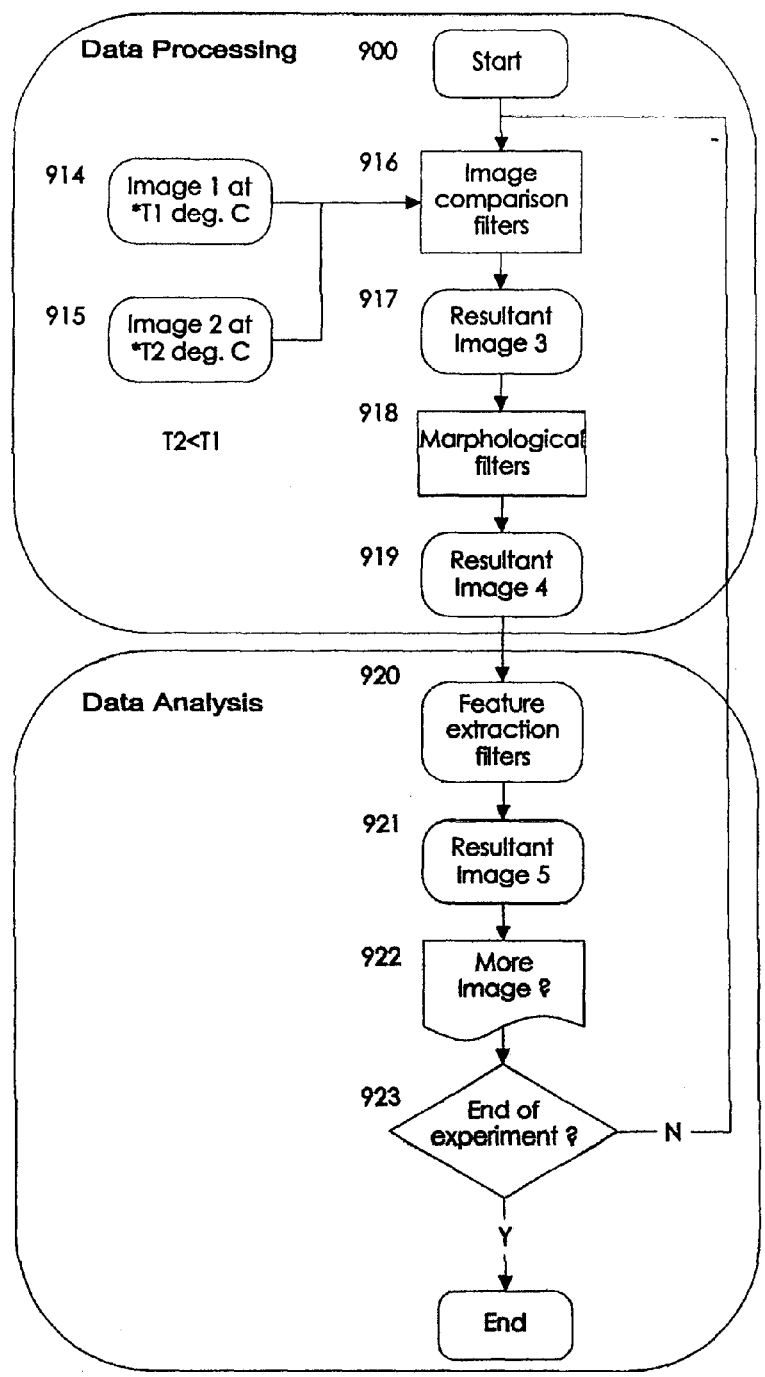

FIG. 11 is a flow chart showing the steps of temperature control to illustrate controlling the cooling rate during testing of samples. Temperature control begins with sensing a temperature T at time t 1000 after at least 3 temperature increment drop. The temperature T is compared to T-3 which is 3 degree increments before the current temperature T. By comparing the two sets of time and temperature, a cooling rate is calculated 1001. If the calculated cooling rate is greater than 6 degrees per minute 1002, cooling is slowed by closing a control valve 1003, and time and temperature are again compared 1000, 1001. If the cooling rate is less than 1 degree per minute 1004, a control valve is opened 1005, and time and temperature are again compared 1000, 1001. If the cooling rate is between 6 degrees per minute and 1 degree per minute, cooling continues at that rate, and time and temperature are again compared 1000, 1001.

An advantage of the invention is computer imaging software which is able to simultaneously capture the images of the samples and record the debonding of samples and the temperatures at which debonding occurs and then automatically calculates the debonding energies. The camera 7 takes snapshots of the samples at each one degree of temperature change. As the samples cool, the camera records the moment of fracture of the film from the substrate and the computer processor records the photo and the temperature at the moment of fracture.

Another advantage of the invention is the complete automation and control of the entire process by computer processor from heating through cooling, image capturing and calculation of debonding energies, then providing the user with graphing of the resultant data in a visual chart for the user.

Calculation of the amount of energy necessary to separate the film layer from the substrate is performed by the computer processor. The measurements of thickness of each sample are inputted into the computer. Using the temperature at which the delaminating occurs, calculation of the fracture energy needed for the thin film or coating to delaminate is accomplished by extracting the applied stress value from the graph of the function of stress over temperature of the epoxy 65.

Characterization of the epoxy is established by stress testing an epoxy coated silicon wafer and graphing the data as a function of stress. Applied stress intensity (Kapp) is a function of stress ( ) over temperature (t) and the square root of the thickness (h) of the epoxy layer divided by two, or: Kapp=(t) (h/2).

The recorded temperature at which delaminating occurs in the sample is used by the computer processor to calculate the critical fracture toughness of the thin film or coating.

If a peeling site is selected, the image processing software will calculate and show the amount of energy needed to separate the film layer from the substrate. An advantage of the invention is the complete automation and control of the entire process by computer from heating through cooling and calculation of debonding energies with graphing of data in a visual chart for the user.

The invention's achievement is that the entire process is automated and controlled by a computer processor 7 which is connected to the temperature control unit 5, the camera 9, the heat exchanger/mixer 12, and the mixer assembly 8.

While the present invention may have been described in terms of several preferred embodiments, there are many alterations, permutations, and equivalents which may fall within the scope of this invention. It should be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An apparatus for analyzing adhesion characteristics of thin films to materials comprising
   a housing;
   a chamber disposed within said housing, said chamber being capable of achieving multiple temperatures;
   at least one sample tray disposed within said chamber for holding material samples;
   a first and second sensor disposed within said housing for providing a first set of sample images and second set of corresponding sample temperatures; and a data correlator coupled to said first and second sensors for correlating a first sample image at a temperature T1 and a second sample image at a temperature T2, wherein T2<T1.

2. An apparatus as recited in claim 1, further comprising at least one light mounted on said housing for illuminating material samples.

3. An apparatus according to claim 2 wherein said light source is an incandescent lamp.

4. An apparatus according to claim 2 wherein said light source is a fluorescent lamp.

5. An apparatus as recited in claim 1, further comprising a temperature control unit coupled to said housing for controlling the temperature of said chamber.

6. An apparatus as recited in claim 5, further comprising a heat exchanger/mixer disposed within said chamber capable of achieving multiple temperatures for varying the temperature of said chamber.

7. An apparatus as recited in claim 6, further comprising mixing control valves coupled to said housing for mixing gas and liquid coolant to vary the temperature of said chamber.

8. An apparatus as recited in claim 1 wherein said first sensor is a thermocouple.

9. An apparatus as recited in claim 1 wherein said second sensor is an image capturing device mounted on said housing for recording images of said samples.

10. An apparatus according to claim 9 wherein said image capturing device is a camera.

11. An apparatus according to claim 9 wherein said image capturing device is a motion camera.

12. An apparatus as recited in claim 9 wherein said image capturing device is a digital camera.

13. An apparatus as recited in claim 9 wherein the data correlator is coupled to said image capturing device, a thermocouple, a heat exchanger/mixer, and mixing control valves.

14. An apparatus as recited in claim 13 wherein said mixing control valves are further coupled to said housing for mixing gas and nitrogen to vary the temperature of said chamber.

15. An apparatus as recited in claim 1, wherein said data correlator includes image analyzing software for processing and correlating images of said samples.

16. An apparatus as recited in claim 1 further comprising convection accelerator holes placed into the body of said sample tray.

17. An apparatus as recited in claim 1 further comprising predistributors inserted into said heat exchanger/mixer.

18. An apparatus according to claim 1 further comprising at least one optical viewing window mounted in said chamber above said sample tray for viewing said material samples.

19. An apparatus as recited in claim 18 wherein said optical viewing window is made of a temperature stable material.

20. An apparatus as recited in claim 18 wherein said optical viewing window is made of Plexiglas.

21. An apparatus as recited in claim 18 wherein said optical viewing window is made of glass.

22. An apparatus as recited in claim 18 wherein said optical viewing window is made of quartz.

* * * * *

UNITED STATES PATENT AND TRADEMARK OFFICE
CERTIFICATE OF CORRECTION

PATENT NO.   : 6,567,541 B1
DATED        : May 20, 2003
INVENTOR(S)  : Phue Van et al.

It is certified that error appears in the above-identified patent and that said Letters Patent is hereby corrected as shown below:

Title page should be deleted and substitute therefore the attached title page.

<u>Drawings,</u>
Delete Figures 1-10 and substitute therefore Figures 1-10 as shown on the attached pages.

Signed and Sealed this

Thirtieth Day of September, 2003

JAMES E. ROGAN
*Director of the United States Patent and Trademark Office*

United States Patent
Van et al.

(10) Patent No.: US 6,567,541 B1
(45) Date of Patent: May 20, 2003

(54) METHOD AND APPARATUS FOR ADHESION TESTING OF THIN FILM MATERIALS

(75) Inventors: Phuc Van, San Jose, CA (US); Yuen Lim, San Jose, CA (US)

(73) Assignee: Ahbee 1, L.P., San Jose, CA (US)

( * ) Notice: Subject to any disclaimer, the term of this patent is extended or adjusted under 35 U.S.C. 154(b) by 0 days.

(21) Appl. No.: 09/512,787

(22) Filed: Feb. 25, 2000

(51) Int. Cl.[7] ................................. G06K 9/00
(52) U.S. Cl. ........................... 382/145; 438/16
(58) Field of Search ............... 382/145; 29/833; 438/16; 118/666, 708, 712, 713; 427/10; 204/298.03; 356/369

(56) References Cited

U.S. PATENT DOCUMENTS

| | | | |
|---|---|---|---|
| 4,177,372 A | * | 12/1979 | Kotera et al. ............ 117/39 |
| 4,905,319 A | * | 2/1990 | Schroder et al. ......... 505/191 |
| 5,143,896 A | * | 9/1992 | Harada et al. ........... 118/708 |
| 5,240,180 A | * | 8/1993 | Feuillerat et al. ....... 239/132.3 |
| 5,955,139 A | * | 9/1999 | Iturralde ................. 427/9 |

FOREIGN PATENT DOCUMENTS

| | | | |
|---|---|---|---|
| GB | 2269799 | * | 2/1994 |
| JP | 3-56846 | * | 3/1991 |
| JP | 2001-220688 | * | 8/2001 |
| WO | WO 98/51754 | * | 11/1998 |

* cited by examiner

Primary Examiner—Samir Ahmed

(57) ABSTRACT

An apparatus for the automatic testing the adhesion characteristics of thin film and coating to silicon wafers, and the processing of the data obtained thereby to present to the user a rapid and accurate forecast of the thin film's behavior in a selected processing environment. The apparatus of the invention heats and cools samples while automatically monitoring for debonding. Information collected from the optical and thermal devices are processed by computer for analysis and recorded for cataloging. Information is collected and processed over time while samples are subjected to selected temperature environments to provide a data base of adhesion characteristics of thin films and coatings.

22 Claims, 12 Drawing Sheets

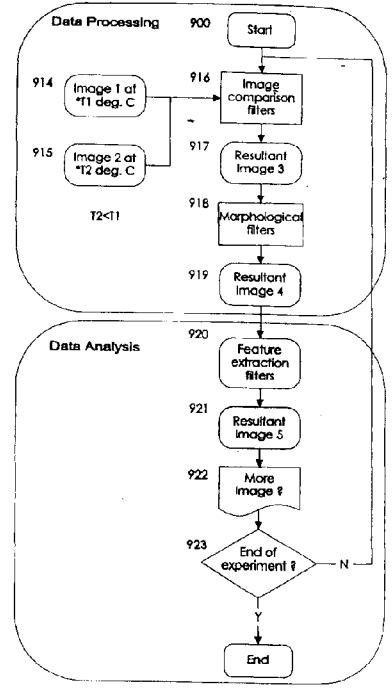

Types of image capturing device

1. Single frame camera like SLR
2. Motion camera like VCR, Camcorder
3. Digital single frame camera
4. Digital motion camera like digital camcorder